(12) United States Patent
Campos

(10) Patent No.: US 10,918,574 B2
(45) Date of Patent: Feb. 16, 2021

(54) MULTI-CHAMBER MEDICAMENT DISPENSING DEVICE

(71) Applicant: Eric Franquez Campos, Fullerton, CA (US)

(72) Inventor: Eric Franquez Campos, Fullerton, CA (US)

(*) Notice: Subject to any disclaimer, the term of this patent is extended or adjusted under 35 U.S.C. 154(b) by 117 days.

(21) Appl. No.: 16/160,673

(22) Filed: Oct. 15, 2018

(65) Prior Publication Data

US 2019/0110954 A1   Apr. 18, 2019

Related U.S. Application Data

(60) Provisional application No. 62/707,006, filed on Oct. 16, 2017.

(51) Int. Cl.
| | |
|---|---|
| *A61J 1/22* | (2006.01) |
| *A61K 36/185* | (2006.01) |
| *A61J 7/00* | (2006.01) |
| *A61J 3/00* | (2006.01) |
| *A61J 1/06* | (2006.01) |

(52) U.S. Cl.
CPC ............. *A61J 1/22* (2013.01); *A61J 3/002* (2013.01); *A61J 7/0084* (2013.01); *A61K 36/185* (2013.01); *A61J 1/06* (2013.01); *A61J 7/0046* (2013.01)

(58) Field of Classification Search
CPC ...... A61M 5/16827; A61M 5/24; A61M 5/28; A61M 5/204; A61M 5/2066; A61M 5/31; A61M 5/30; A61M 2005/3126; A61M 5/19; A61M 2005/2403; A61M 2210/0625; A61J 1/22; A61J 7/0084; A61J 1/06; A61J 1/2089; B05C 17/01
See application file for complete search history.

(56) References Cited

U.S. PATENT DOCUMENTS

| | | | | |
|---|---|---|---|---|
| 6,116,900 | A * | 9/2000 | Ostler | A61C 19/066 433/89 |
| 7,416,540 | B2 * | 8/2008 | Edwards | A61M 5/2033 604/144 |
| 2008/0262469 | A1 * | 10/2008 | Brister | A61B 5/0002 604/504 |
| 2012/0330228 | A1 * | 12/2012 | Day | A61M 5/31546 604/82 |
| 2017/0030882 | A1 * | 2/2017 | Skoda | G01N 33/15 |
| 2019/0111219 | A1 * | 4/2019 | Campos | A61M 11/041 |

* cited by examiner

*Primary Examiner* — Nathan R Price
*Assistant Examiner* — Melissa A Snyder
(74) *Attorney, Agent, or Firm* — Acuity IP, LLC; Nathan S. Cassell

(57) ABSTRACT

A handheld Multi-chamber dispensing system comprising a connecting body configured for accepting multiple liquid compound vials/cartridges for attachment. A triple location within the connecting body with at least three separate reservoirs. The modules/vials containing at least one dose of a liquid compound and configured for fluid communication with a delivery spout. A microprocessor controlled circuit that serves as a controller for the multiple reservoirs of liquid compounds.

13 Claims, 5 Drawing Sheets

MULTI-CHAMBER MEDICAMENT DISPENSING DEVICE

TECHNICAL FIELD

This invention relates to a medical dispensing device and method of delivering two or more medicaments or agents from isolated reservoirs using a dispensing device with two or more separate chambers or reservoirs. More specifically, the present invention is directed to a dual or Multi-chamber module comprising a separate reservoir housing a medicament and at least a second separate reservoir housing another medicament. The separate chambers may provide a user an option of micro-dosing each medicament to a custom level dictated by the user's tolerance or health care professional. The medicaments may be available in two or more chambers each containing independent (single molecule compounds) or pre-mixed (co-formulated multiple molecule compounds). Additionally, the present invention may be optimized for a specific target patient group through control of a dosing and definition of a therapeutic profile.

BACKGROUND

*Cannabis* is a substance derived from the hemp plant (*Cannabis indica* or *Cannabis sativa*). Derived materials include cannabinoids, terpenes and flavonoids. In this specification these, and other derivatives, are referred to generically as *cannabis* molecules.

After decarboxylation, Cannabidiol (CBD) and tetrahydrocannabinol (THC) are the two main ingredients in the *cannabis* plant. Both CBD and THC belong to a unique class of compounds known as cannabinoids.

THC is probably best known for being the psychoactive ingredient in *cannabis*. CBD, however, is non-psychoactive. In other words, CBD can't get you high. While disappointing to recreational users, this unique feature of CBD is what makes it appealing as a medicine.

Certain mood disorders require treatment using one or more different medicaments. The sensitivity to drugs for people with mood disorders is common and there is no "one size fits all" solution to the problem. Cannabinoid treatment for mood disorders is a relatively new science, however, it is known that too much *cannabis* can negatively affect the condition and patient being treated.

Patients prefer and/or require cannabinoid and terpene compounds to be delivered in a specific relationship with each other in order to deliver the optimum therapeutic dose. This invention is of particular benefit where combination therapy is desirable, but not possible in a single formulation for reasons such as, but not limited to, stability, dose amount, dose control and compromised therapeutic performance and toxicology.

Micro-dosing *cannabis* involves taking a very measured micro-dose of THC, the psychoactive ingredient, and a measured micro-dose of CBD, the non-psychoactive therapeutic ingredient in *cannabis*.

With micro-dosing, users get the maximum benefit from the minimum amount, without becoming overly affected.

Right now, anyone that wants to micro-dose faces two hurdles: finding the right minimum dose and finding products that will deliver it.

The ability to set a dose of one cannabinoid (such as THC) to a custom level and also having ability to custom set the dose of a separate cannabinoid or mixture of cannabinoids (such as CBD) may give the healthcare professionals and patients the flexibility to titrate the medicinal compounds up or down with more precision. The present invention may give the opportunity for precisely varying the quantity of one or both reservoirs of cannabinoids. For example, one fluid quantity may be varied by changing the programming of the dispensing device. This may be completed by dialing a user variable dose or changing the device's "fixed" dose. The second medicament quantity may be changed exactly the same way. The user or healthcare professional may then select the most appropriate micro-dosing quantity for a particular treatment regime.

Cannabinoids (CBD, THC, etc.) are hydrophobic substances. They can, however, be formulated to be water-compatible and appear water-soluble.

CBD, THC and other oils can, however, be made water-compatible if they are formulated as oil-in-water nanoemulsions, which are stable and visually homogeneous oil/water mixtures. Nanoemulsions can be prepared in concentrated forms (tens of mg/ml) that are fully miscible with water and, therefore, appear water-soluble. In addition, nanoemulsions can be made translucent and practically tasteless, which means that they can be mixed into water without compromising its optical clarity or taste.

Nanoemulsions are beneficial because they are easily mixed into beverages, translucent, low-taste and safe for consumption, exceptionally high bioavailability, fast onset of action, and stable blood level and high CBD/THC loading capacity.

The present invention combines the Multi-chamber dispensing device with nanoemulsion technology to provide a precise, high water soluble and bioavailable product for medicinal *cannabis* consumption.

These and other advantages will become evident from the following more detailed description of the invention.

SUMMARY OF THE INVENTION

The present invention discloses modules, systems and methods that allow for the dose controlled dual or multiple dispensing of medicaments within a single device. Preferably, such a system includes two dispensing spouts each individually attached to separate liquid chambers. Each individual chamber is attached to a stepper motor that is linked to software-driven motor control for precise dispensing of liquid compounds.

A user can set and dispense a pre-determined dose of medicaments through one chamber and set a different dose to dispense from the other chamber. Preferably, the dual compound dispenser interface may be programmed to dispense each chamber with a preset micro-dose. The multiple chambered dose setter controls step motors of the device such that a predefined quantity of medicaments is delivered when each chambered dose is set and dispensed through the dual compound dispense interface.

BRIEF DESCRIPTION OF DRAWINGS

The present invention will become more fully understood from the detailed description and accompanying drawings, which are not to scale.

DETAILED DESCRIPTION

In the Summary above and in this Detailed Description, and the claims below, and in the accompanying drawings, reference is made to particular features of the invention. It is to be understood that the disclosure of the invention in this specification includes all possible combinations of such particular features. For example, where a particular feature is disclosed in the context of a particular aspect or embodiment of the invention, or a particular claim, that feature can also be used—to the extent possible—in combination with and/or in the context of other particular aspects and embodiments of the invention, and in the invention generally The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also contain one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range including that number (which may be a range having an upper limit or no upper limit, depending on the variable being defined). For example, "at least 1" means 1 or more than 1. The term "at most" followed by a number is used herein to denote the end of a range, including that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)," this means a range whose limits include both numbers. For example, "25 to 100" means a range whose lower limit is 25 and upper limit is 100, and includes both 25 and 100.

The present invention is directed to a system for administering a precise, customized dose of two or more medicaments. Setting the dose of the medicaments by the user gives the patient more reliable control over the therapeutic outcome of micro-dosed therapy. These combined variable doses are preferable over single dose therapy. In a preferred arrangement, the compound dispensing interface comprises a hollow spout for delivery of liquid compounds. The system may include touch pad interface for simple UP and DOWN control of dosing device.

Figure 1:
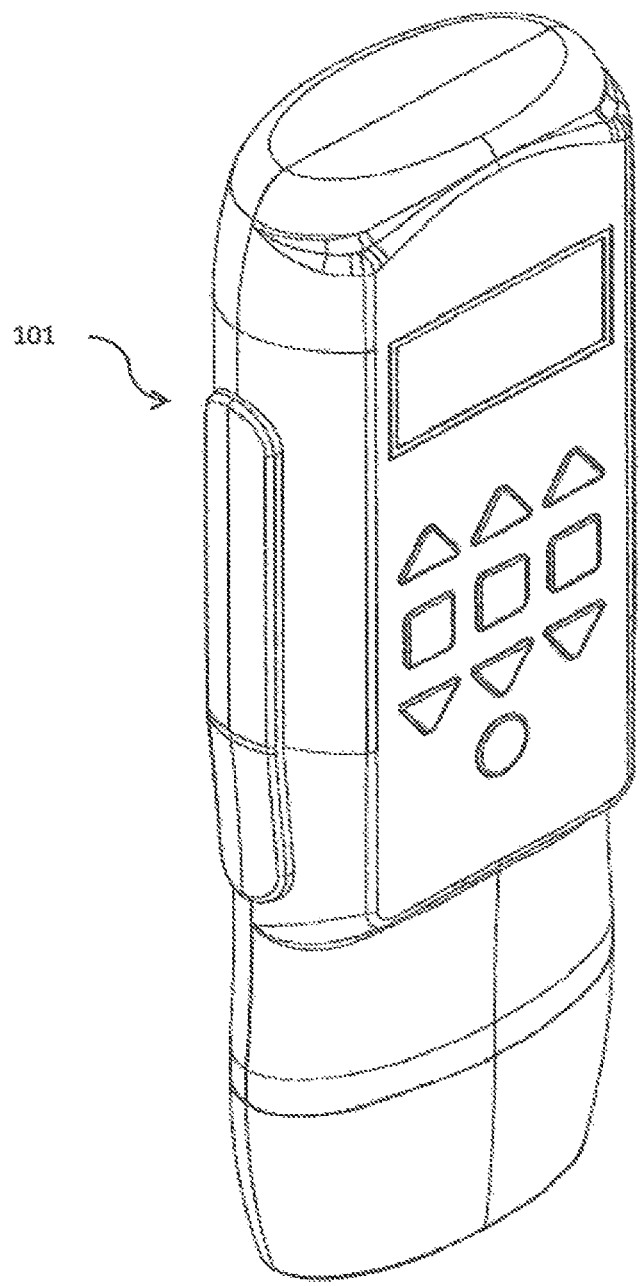
FIG. 1 illustrates an exploded view of the multi-chamber dispensing device that can be attached to three compound delivery vials.

FIG. 1 shows a complete assembled multi-chamber medicament dispensing device 101.

Figure 2:
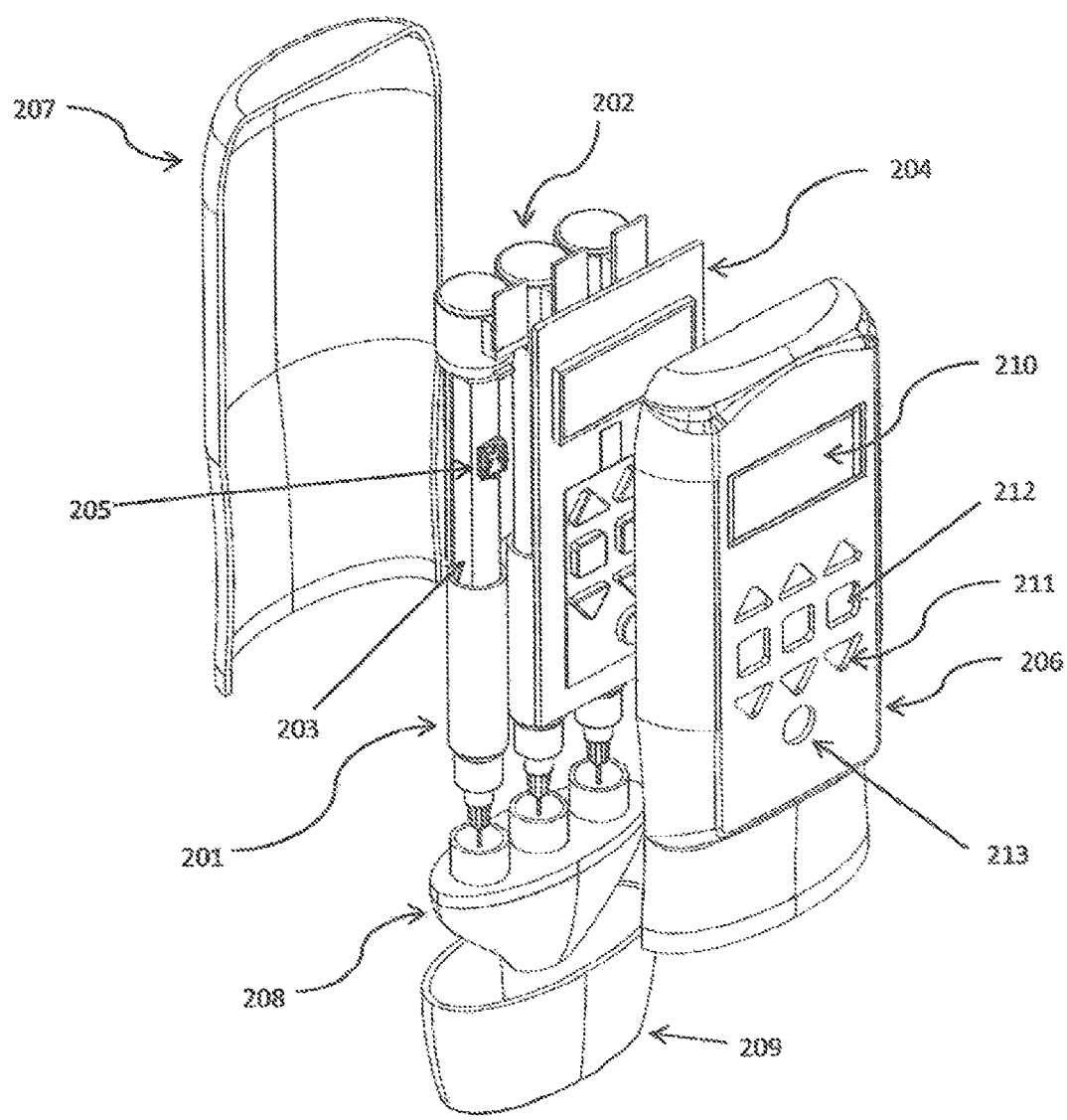
FIG. 2 illustrates a cross-sectional view of the multi-chamber dispensing device attached to the compound delivery vials illustrated in FIG. 1.

FIG. 2 shows an exploded view of a multi-chamber medicament dispensing device. FIG. 2 shows three medicament vials 201 connected to stepper motors 202, a plunger 203 at the end of each stepper motor 202, a circuit board assembly 204, a charging port 205, a front housing 206 and rear housing 207, a dispensing spout 208 at the end of each vial, an end cap 209, an indicator screen 210, adjustment UP and DOWN keypad buttons 211, a dispensing button 212, and an ON/OFF button 213.

The front housing 206 and rear housing 207 cover the circuit board assembly 204, and the stepper motors 202 but leave the tips of vials 201 exposed for simple vial replacement. The end cap 209 covers the cylindrical shaped vials 201 after each use.

Externally the ON/OFF button 213 controls the power of device which times out after 30 seconds of non-use. The indicator screens 210 show the amount of the dose chosen by the UP and DOWN keypad buttons 211. The dispensing button 212 activates the dispensing process which precisely controls all three chambers of the medicaments.

Figure 3:
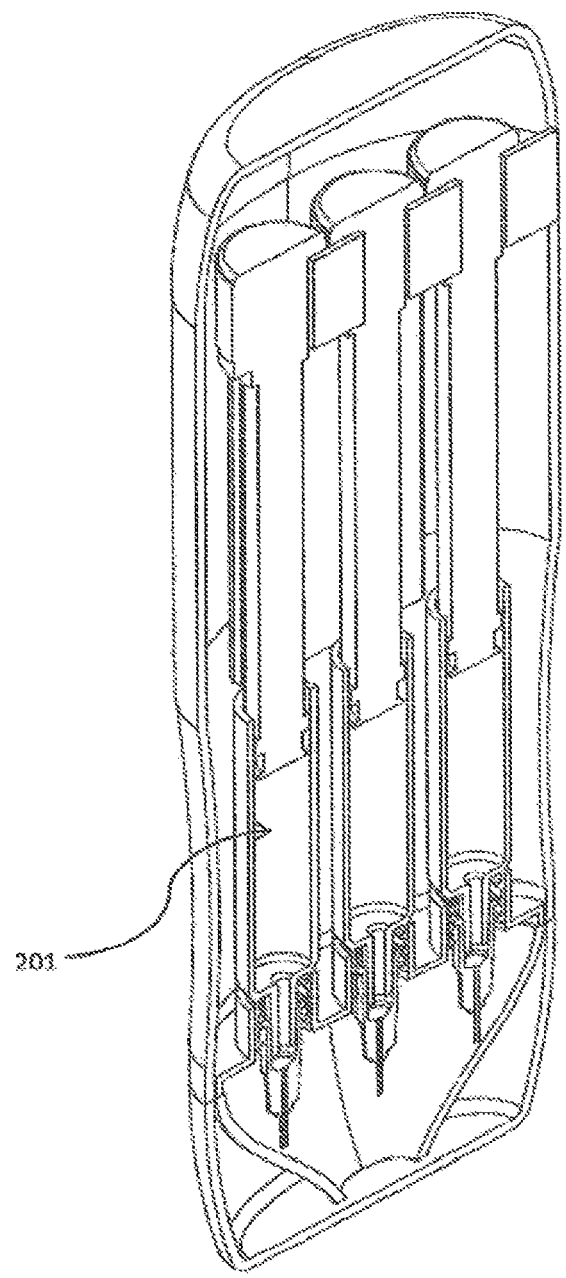
FIG. 3 illustrates a close up exploded view of vials of the multi-chamber dispensing device in FIG. 1.

FIG. 3 illustrates a cross-sectional view of the multi-chamber medicament dispensing device and the compound delivery vials 201 illustrated in FIG. 2.

Figure 4:
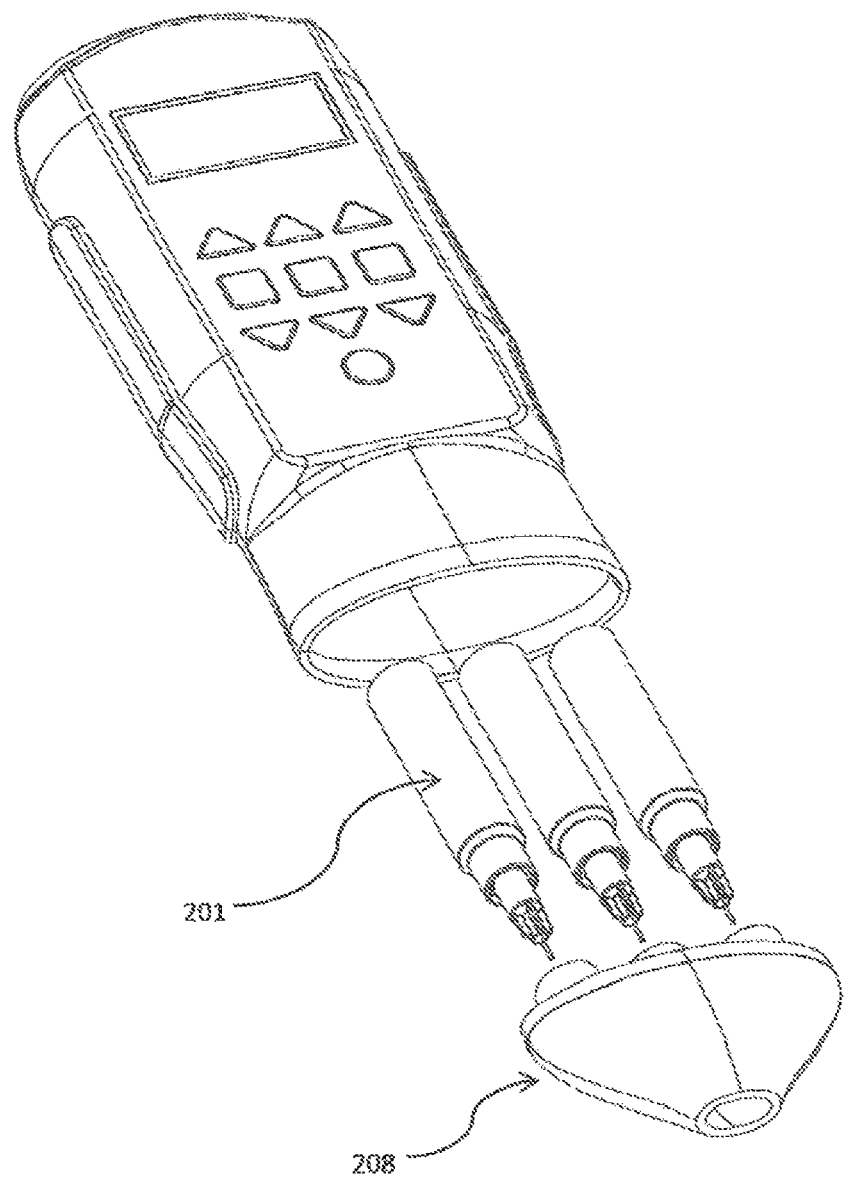
FIG. 4 illustrates the three medicament vials with spouts with three vials and dispensing spout, 208, removed from the multi-chamber dispensing delivery device.

FIG. 4 illustrates a perspective exploded view of the vials 201 of FIG. 2. The dispensing spout 208 of FIG. 2 may be screwed unto the end of the vial 201 for a secure fit that is ready to dispense medicaments. FIG. 4 shows the device with spout 208 of FIG. 2 removed from the device. Potential materials that this stopper could include, but are not limited to, are TPE (Thermoplastic Elastomers), Liquid Silicone Rubber (LSR) and natural rubbers. Alternative materials, including Low-density Polyethylene (LDPE) or Linear low-density Polyethylene (LLDPE) are also possible.

Figure 5:
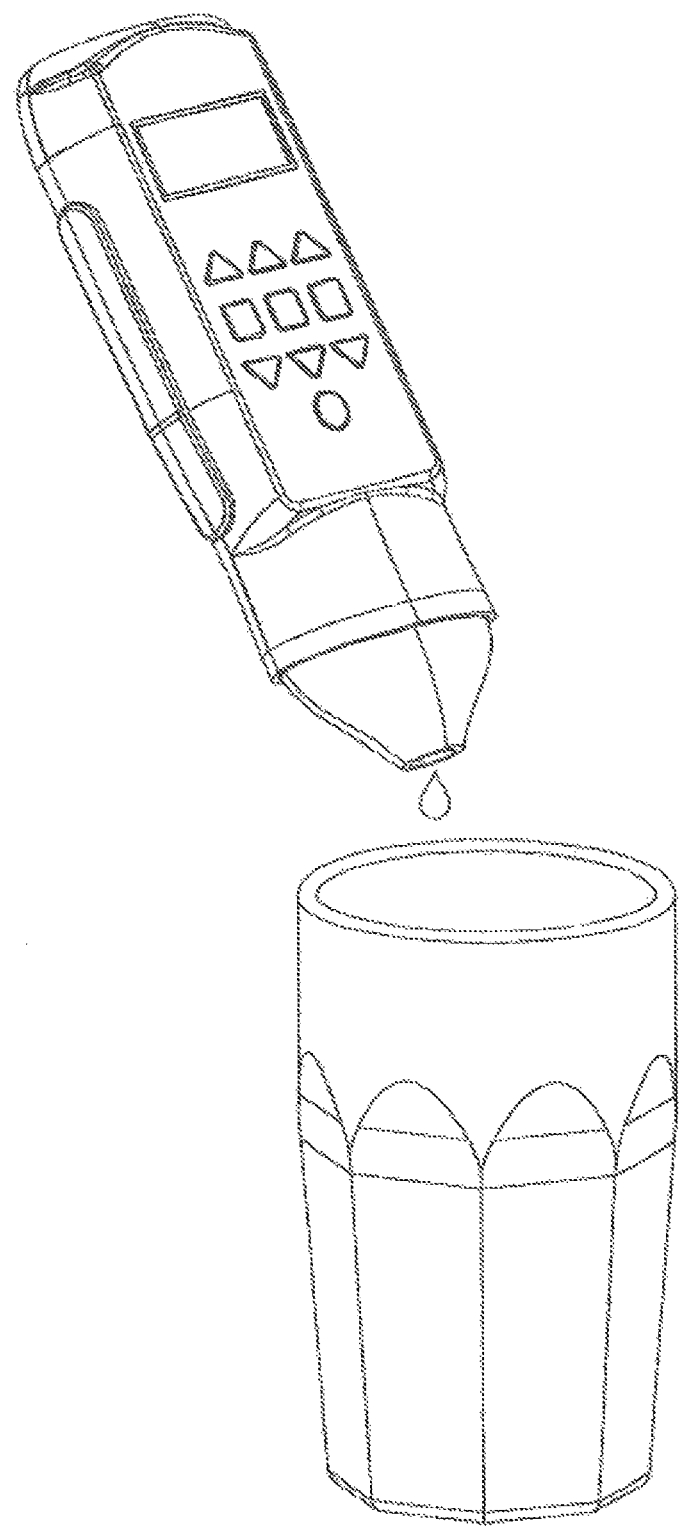
FIG. 5 illustrates a completely assembled multi-chamber dispensing device illustrated in FIG. 1

FIG. 5 illustrates the multi-chamber medicament dispensing device with dispensing spout 208 illustrated in FIG. 2.

FIG. 6 illustrates the face view of the multi-chamber medicament dispensing device showing the UP and DOWN dose control buttons 211 with numbered LED display 210 of FIG. 2.

Where the triple dispenser device 10 comprises dose setter buttons 100, a dose of the dispensing device 10 may then be set using a dose setter buttons 100 in the normal manner (e.g., by dialing out the appropriate number of units). Dispensation of the liquid compound may then be achieved by dispensing water soluble liquid contents via activation of the GO button 110 on device 10. In a preferred embodiment, the dose buttons 100 are operably connected to PCB assembly that engages each stepper motor to push on reservoirs of each vial of the liquid medicaments.

As mentioned above, in any of the methods described herein, appropriate liquid medicaments to be infused may be used. In general, the water soluble liquid medicaments may be cannabinoid oils or terpenes. The liquid medicament may comprise any active ingredient(s). For example, the liquid medicament may comprise a botanical. The medicament may comprise a cannabinoid. The medicament may comprise one or more of: cetirizine, ibuprofen, naproxen, omeprazole, doxylamine, diphenhydramine, melatonin, or meclizine. The medicament may comprise one or more of: a polyphonel, short chain fatty acids, medium chain fatty acids, long chain fatty acids, a green tea catechin, caffeine, a phenol, a glycoside, a labdane diterpenoid, yohimbine, a proanthocyanidin, terpene glycoside, an omega fatty acid, echinacoside, an alkaloid, isovaleric acid, a terpene, gamma-aminobutyric acid, a *senna* glycoside, cinnamaldehyde, or Vitamin D.

Although the preceding description contains significant detail in relation to the preferred embodiment, it should not be construed as limiting the scope of the invention but rather as providing illustrations of the preferred embodiments.

By defining the therapeutic relationship between the individual cannabinoid compounds our delivery device would help ensure that a patient/user receives the optimum therapeutic combination dose from a multi-cannabinoid compound device without the inherent risks associated with single dose devices. The cannabinoids and terpenes can be water soluble fluids that make it easy to dispense, dissolve and mix into beverage of choice.

This invention is of particular benefit to patients with THC sensitivity and who are not sure of what dose will work best for their condition. Giving the user the ability to titrate up or down in micro-doses insures better patient tolerance and therapeutic benefits. This invention eliminates the need for trial and error single dose consumption that current dropper based systems offer. This invention is also of particular benefit to patients experiencing the fear or phobia associated with THC consumption.

In the preferred embodiment, the primary delivery device has replaceable modules or vials and can be used more than once and therefore is multi-use. It is possible to have a selection of different cannabinoid vials/modules for various conditions that could be prescribed to patients.

In a further embodiment the delivery system comprises a software driven, battery powered printed circuit board coupled to two or more stepper motors with a plunging feature allowing for the software control and tracking of each precise dose.

In a further embodiment the medicament delivery system according to the invention disclosed herein comprises a mechanical non-motorized stepper feature, wherein both chambers have a mechanical plunger feature that are part of the medicament delivery device according the invention in this disclosure.

In a further embodiment, the dispenser unit has an interface to cell phone or tablet devices, such as Wi-Fi or Bluetooth if wireless, USB or Ethernet if wired; whereby a mobile device becomes the controlling device for the dispenser. The actual method or backbone for interface to the controlling device is not critical to the invention, and should not be used to narrow rights to future claims.

Related applications include patent applications 200400749321 and WO2010129835A2, and U.S. Pat. Nos. 6,159,188A and 9,884,336. These references do not teach the entire present invention.

The invention claimed is:

1. A multi-chamber multi-cannabinoid medicament dispensing device, comprising:
    a first medicament vial having a tip, and containing a first nanoemulsion comprising a first cannabinoid, the first cannabinoid comprising a non-psychoactive *Cannabis* molecule;
    a first plunger configured to dispense an amount of the first nanoemulsion from the tip of the first medicament vial;
    a second medicament vial having a tip, and containing a second nanoemulsion comprising a second cannabinoid, the second cannabinoid comprising a psychoactive *Cannabis* molecule;
    a second plunger configured to dispense an amount of the second nanoemulsion from the tip of the second medicament vial;
    a front housing;
    a rear housing coupled with the front housing, wherein the coupled front housing and rear housing contain the first plunger and the second plunger; and
    a dispensing spout coupled with the front housing and the rear housing, the dispensing spout comprising a first proximal aperture, a second proximal aperture, an interior chamber, and a distal aperture;
    wherein the first medicament vial is positioned partially within the first proximal aperture of the dispensing spout and the second medicament vial is positioned partially within the second proximal aperture of the dispensing spout, and
    wherein the tip of the first medicament vial is positioned within the interior chamber of the dispensing spout and the tip of the second medicament vial is positioned within the interior chamber of the dispensing spout, such that the amount of the first nanoemulsion is dispensed from the tip of the first medicament vial into the interior chamber, and the amount of second nanoemulsion is dispensed from the tip of the second medicament vial into the interior chamber to combine with the dispensed amount of the first nanoemulsion within the interior chamber, and
    wherein the distal aperture of the dispensing spout is configured to allow the combination of the dispensed amount of the first nanoemulsion and the dispensed amount of the second nanoemulsion to pass from the interior chamber of the dispensing spout therethrough.

2. The device of claim 1, further comprising a circuit board assembly, a first motor coupled with the first plunger, and a second motor coupled with the second plunger, wherein the circuit board assembly engages the first motor and the second motor.

3. The device of claim 2, wherein the front housing and the rear housing cover the circuit board assembly and leave the tip of the first medicament vial and the tip of the second medicament vial exposed, to facilitate removal of the first medicament vial and the second medicament vial from the multi-chamber multi-cannabinoid medicament dispensing device for replacement.

4. The device of claim 2, further comprising UP and DOWN keypad buttons for the first medicament vial operably connected to the circuit board assembly and UP and DOWN keypad buttons for the second medicament vial operably connected to the circuit board assembly, and wherein the UP and DOWN keypad buttons for the first medicament vial and the UP and DOWN keypad buttons for the second medicament vial enable selection of a desired relationship between a volume of the first nanoemulsion containing the non-psychoactive *Cannabis* molecule and a volume of the second nanoemulsion containing the psychoactive *Cannabis* molecule wherein the modules provide a precise volume of medicaments.

5. The device of claim 1, wherein the non-psychoactive *Cannabis* molecule is cannabidiol and the psychoactive *Cannabis* molecule is tetrahydrocannabinol.

6. The device of claim 1, further comprising a circuit board assembly that tracks the dispensed amount of the first nanoemulsion and the dispensed amount of the second nanoemulsion.

7. A method of dispensing a combination dose from a handheld multi-chamber multi-cannabinoid compound device, the method comprising:
    holding the handheld multi-chamber multi-cannabinoid compound device by hand, wherein the multi-chamber multi-cannabinoid compound device comprises:
        a first medicament vial having a tip, and containing a first nanoemulsion comprising a first cannabinoid, the first cannabinoid comprising a non-psychoactive *Cannabis* molecule;
        a first plunger configured to dispense an amount of the first nanoemulsion from the tip of the first medicament vial;

a second medicament vial having a tip, and containing a second nanoemulsion comprising a second cannabinoid, the second cannabinoid comprising a psychoactive *Cannabis* molecule;

a second plunger configured to dispense an amount of the second nanoemulsion from the tip of the second medicament vial;

a front housing;

a rear housing coupled with the front housing, wherein the coupled front housing and rear housing contain the first plunger and the second plunger; and a dispensing spout coupled with the front housing and the rear housing, the dispensing spout comprising a first proximal aperture, a second proximal aperture, an interior chamber, and a distal aperture;

wherein the first medicament vial is positioned partially within the first proximal aperture of the dispensing spout and the second medicament vial is positioned partially within the second proximal aperture of the dispensing spout, and wherein the tip of the first medicament vial is positioned within the interior chamber of the dispensing spout and the tip of the second medicament vial is positioned within the interior chamber of the dispensing spout, such that the amount of the first nanoemulsion can be dispensed from the tip of the first medicament vial into the interior chamber, and the amount of second nanoemulsion can be dispensed from the tip of the second medicament vial into the interior chamber to combine with the dispensed amount of the first nanoemulsion within the interior chamber, wherein the distal aperture of the dispensing spout is configured to allow the combination dose to pass from the interior chamber of the dispensing spout therethrough, and wherein the combination dose comprises the combination of the dispensed amount of the first nanoemulsion and the dispensed amount of the second nanoemulsion;

activating the first plunger to dispense the amount of the first nanoemulsion from the tip of the first medicament vial into the interior chamber of the dispensing spout;

activating the second plunger to dispense the amount of the second nanoemulsion from the tip of the second medicament vial into the interior chamber of the dispensing spout to combine with the dispensed amount of the first nanoemulsion within the interior chamber to form the combination dose; and allowing the combination dose to pass from the interior chamber of the dispensing spout through the distal aperture of the dispensing spout.

8. The method of claim 7, further comprising positioning the handheld multi-chamber multi cannabinoid compound device over a drinking glass so that the combination dose passes through the distal aperture of the dispensing spout and into the drinking glass.

9. The method of claim 7, wherein the handheld multi-chamber multi cannabinoid compound device further comprises a circuit board assembly, a first motor coupled with the first plunger, and a second motor coupled with the second plunger, and wherein the circuit board assembly engages the first motor and the second motor.

10. The method of claim 9, wherein the front housing and the rear housing cover the circuit board assembly and leave the tip of the first medicament vial and the tip of the second medicament vial exposed, the method further comprising removing the first medicament vial and the second medicament vial from the handheld multi-chamber multi cannabinoid compound device.

11. The method of claim 9, wherein the handheld multi-chamber multi cannabinoid compound device further comprises UP and DOWN keypad buttons for the first medicament vial operably connected to the circuit board assembly and UP and DOWN keypad buttons for the second medicament vial operably connected to the circuit board assembly, and wherein the UP and DOWN keypad buttons for the first medicament vial and the UP and DOWN keypad buttons for the second medicament vial enable selection of a desired relationship between a volume of the first nanoemulsion containing the non-psychoactive *Cannabis* molecule and a volume of the second nanoemulsion containing the psychoactive *Cannabis* molecule.

12. The method of claim 7, wherein the non-psychoactive *Cannabis* molecule is cannabidiol and the psychoactive *Cannabis* molecule is tetrahydrocannabinol.

13. The method of claim 7, wherein the handheld multi-chamber multi cannabinoid compound device further comprises a circuit board assembly that tracks the dispensed amount of the first nanoemulsion and the dispensed amount of the second nanoemulsion.

\* \* \* \* \*